United States Patent [19]

Aegidius

[11] 3,995,495
[45] Dec. 7, 1976

[54] METHOD AND AN APPARATUS FOR TAKING OUT AN AVERAGE MILK SAMPLE PROPORTIONAL TO THE YIELD OBTAINED IN THE MILKING OF A COW

[75] Inventor: Poul Erik Aegidius, Helsinge, Denmark

[73] Assignee: N.K. Verwaltungs AG, Zug, Switzerland

[22] Filed: July 31, 1975

[21] Appl. No.: 600,552

[52] U.S. Cl. .............................................. 73/422 R
[51] Int. Cl.² ......................................... G01N 1/18
[58] Field of Search ............. 73/421 A, 422 R, 202; 137/101

[56] References Cited
UNITED STATES PATENTS

| | | | |
|---|---|---|---|
| 1,121,246 | 12/1914 | Hinman | 73/421 A |
| 2,800,797 | 7/1957 | Honstead | 73/421 A |
| 3,088,316 | 5/1963 | Hutchings | 73/202 |
| 3,349,618 | 10/1967 | Maxwell | 73/202 |
| 3,481,197 | 12/1969 | Wenham | 73/202 |

FOREIGN PATENTS OR APPLICATIONS 879,026   6/1953   Germany ....................... 73/421 A

*Primary Examiner*—S. Clement Swisher
*Attorney, Agent, or Firm*—Ladas, Parry, Von Gehr, Goldsmith & Deschamps

[57] ABSTRACT

An apparatus for taking out an average sample of milk proportional to the yield from the milking of a cow. The apparatus comprises a primary sampling system and a secondary sampling system. The primary sampling system has a chamber into which milk is sucked during the milking of the cow through a first tube terminating at a distance from a superimposed circular cylinder the bottom of which forms a substantially horizontal circular distributor surface which spreads the milk to form a film. A fraction of the film is caught between a first pair of knives, which are not integral with the distributor surface, and passed through a normally open valve into a collecting cup, while the major part of the milk leaves the chamber through a discharge tube in the bottom of the chamber. The secondary sampling system is adapted on completion of the milking to suck the milk from the collecting cup upwards into the chamber through a second tube extending from the bottom of the collecting cup and terminating at a distance from a superimposed second circular cylinder the bottom of which forms a second substantially horizontal circular distribution surface which spreads the milk to form a film. A fraction of that film is caught between a second pair of knives, which are not integral with the second distributor surface, and led down into a test cup, while the major part of the milk from the collecting cup leaves the chamber through the discharge tube in the bottom of the chamber.

11 Claims, 6 Drawing Figures

METHOD AND AN APPARATUS FOR TAKING OUT AN AVERAGE MILK SAMPLE PROPORTIONAL TO THE YIELD OBTAINED IN THE MILKING OF A COW

BACKGROUND OF THE INVENTION

1. Field of the Invention This invention relates to a method and an apparatus for taking out an average milk sample proportional to the yield obtained in the milking of a cow.

The milk is transported from the cow's teats by means of vacuum. The measuring apparatus is inserted in the tube leading from the teat cups to the milk line, from which the milk is sucked into the collection tank.

To facilitate the transport of the milk from the milking unit to the milk line and further to the tank without excessive vacuum drop the milking unit is provided with vent hole through which a suitable quantity of air is sucked in together with the milk, normally of the order of 10 liters of air per minute. On completion of the milking large amounts of false air will often enter at the teats on account of their getting slack. These amounts may often be considerably above for instance 10 liters per minute.

Cows milk at widely different rates, varying from nought to about 10 liters of milk per minute. The milking rate varies (drops) during the milking process.

Apparatus for measuring the milk yield of a cow are generally arranged to draw off a sample during the milking which is approximately proportional to the amount of milk flowing through the system. By measuring the quantity of the sample it will thus be possible to determine the amount of milk that has passed through the apparatus, i.e. the yield obtained from the cow who has been milked. The measurement of the quantity of the sample is generally performed volumetrically by the reading of the scale of a cylindrical tube in which the sample is collected.

2. Description of Prior Art

A proportional sampling from the passing milk may be performed in several ways, but in a conventional procedure used in several types of apparatus the inflowing milk is distributed evenly over a surface, for instance the internal surface of a cylindrical chamber. Such an apparatus is known for instance from the specification of British Pat. No. 1,095,708. Part of the milk distributed in the chamber is received of a funnel the transverse area of which is a certain fraction of the entire transverse area of the cylindrical chamber, and from this funnel the milk sample flows into the metering cylinder where the yield can be read on a scale. The measuring accuracy is determined by the uniformity with which the milk flow is distributed over the internal surface of the cylindrical chamber.

A high milking rate and a low content of air in the milk will give an ample filling of the apparatus and consequently an even distribution of milk over the spreading surface.

Problems of measuring accuracy will arise specifically when the milking rate is low and considerable amounts of air are transported with the milk in consequence of the said influx of false air. In certain milking systems the air intake in the milking unit is considerable. Where such a milking system is combined with slowly milking cows the reading of the apparatus will be too low (about 10–15%, dependent on conditions).

SUMMARY OF INVENTION

Hence, it is an object of the present invention to provide a new method and a new and improved apparatus of the said type in which the measuring accuracy is greater also during the said unfavorable milking conditions.

To be able to produce an accurate measurement the apparatus must also be positioned with the proper orientation in relation to the vertical, since otherwise the distribution of the milk over the spreading surface will be uneven. This is no problem in milking parlours where the milking system is a permanent installation and where the cows may pass through of the stalls as their turn for milking comes. Here the measuring apparatus is placed in a permanently fixed clamp that has been accurately adjusted by means of a spirit level. In barns where the cows are tethered and where the milking machine with measuring apparatus is moved from cow to cow it is much more difficult to ensure an accurate vertical position of the apparatus in every case.

Another object of the invention therefore is to provide an apparatus which is less sensitive to errors of inclination.

Other and further objects will be pointed out hereafter and will be more particularly delineated in the appended claims.

The invention will be described below with reference to the drawing, wherein

DESCRIPTION OF THE PREFERRED EMBODIMENT

Figure 1:
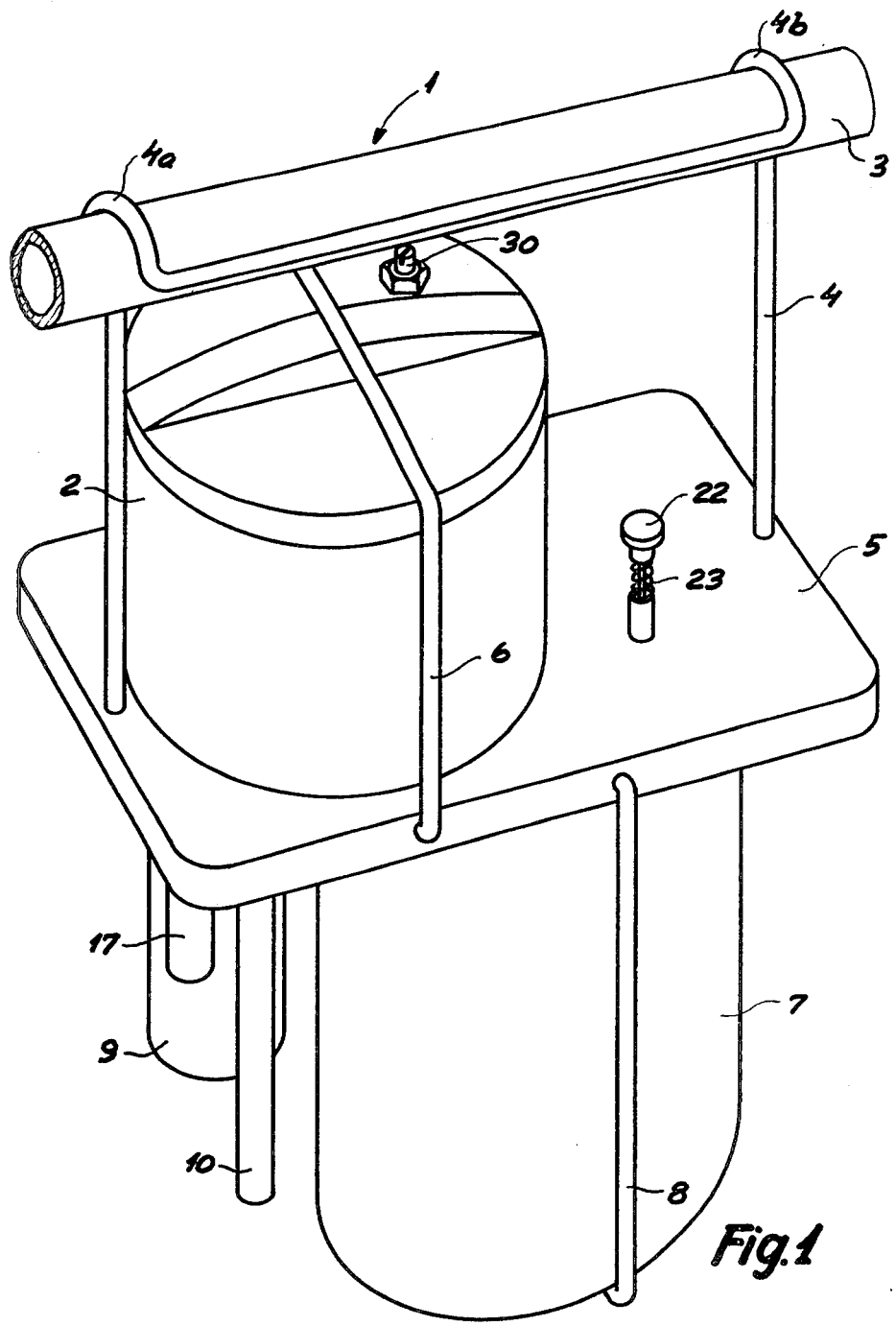
FIG. 1 presents a perspective view of an embodiment of the apparatus according to the invention.
Figure 2:
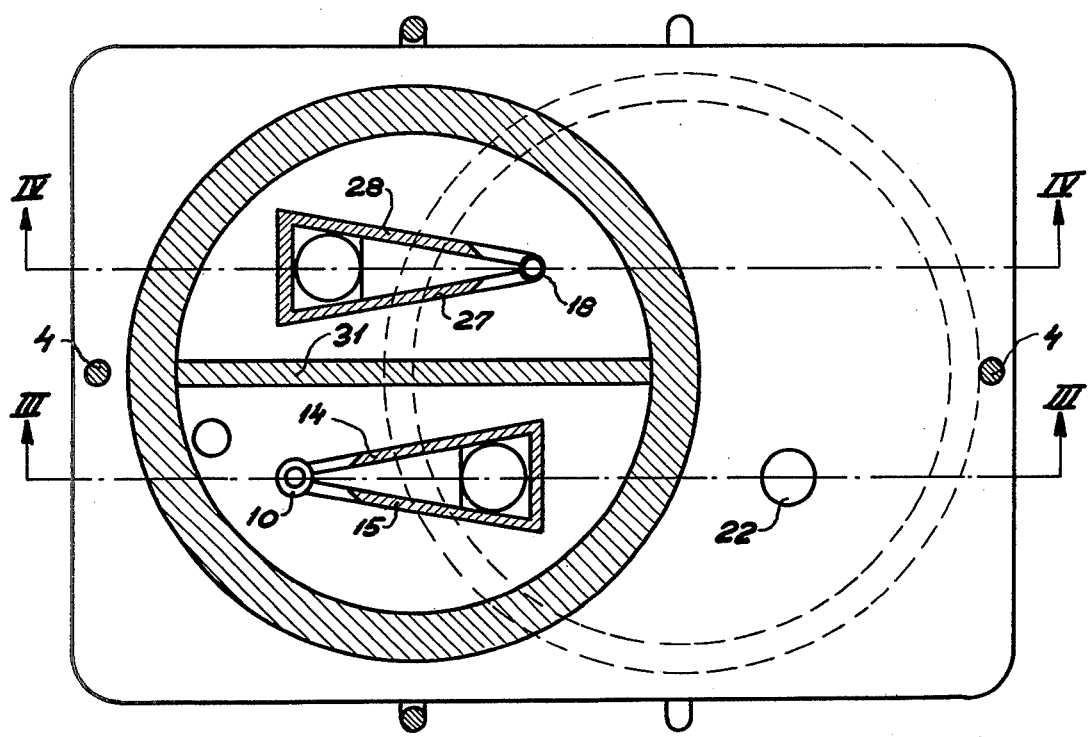
FIG. 2 is the same apparatus viewed from above in section along the line II—II.

The apparatus 1 illustrated in FIG. 1 has a common chamber 2 for a primary (FIG. 3) and a secondary (FIG. 4) sampling system which will be described in greater detail later.

The apparatus is preferably suspended on the milk line 3 extending horizontally in the milking parlour by means of a suspension clamp 4 secured to a base plate 5 below the chamber 2. A clamp 6 holds the cylindrical wall and the cover of the chamber 2 clamped firmly and tightly against the base plate 5. Under the base plate 5 are secured a collecting cup 7 by means of a clamp 8 and a sampling cup 9 by means of a bayonet clamp (not shown).

Figure 3:
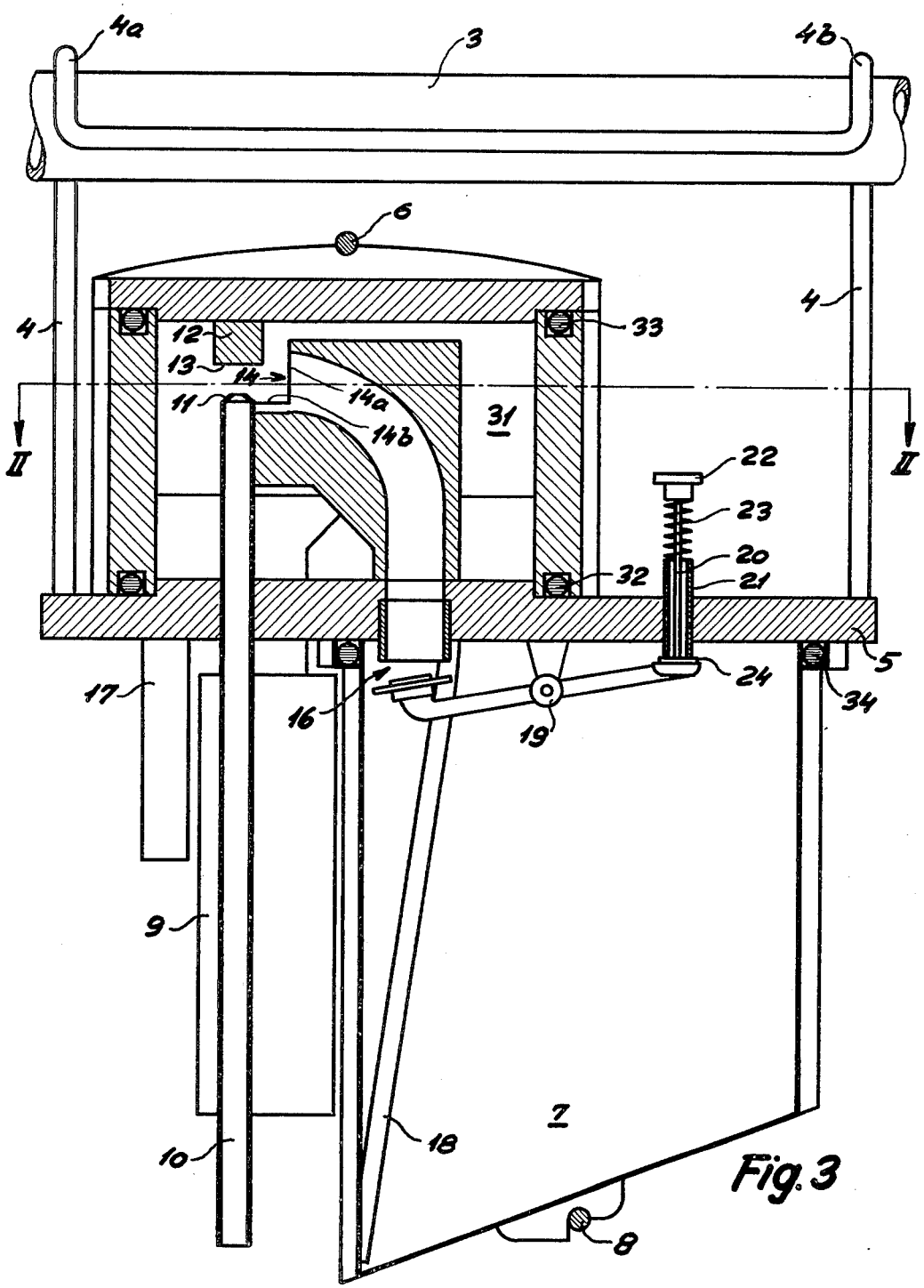
FIG. 3 shows a section along the line III—III in FIG. 2, FIG. 4 a section along the line IV—IV in FIG. 2.

The primary sampling system is shown specifically in FIG. 3. The interior of the chamber 2 communicates through a first tube 10 with a milking unit (not shown) from which the milk as a result of the milking vacuum in the chamber 2 flows upwards through the tube 10 and a restriction 11 at the upper end thereof. When leaving the tube the milk jet hits a cylinder 12 the underside of which forms a horizontal distributor surface 13 from which the milk spreads in a thin horizontal film that is distributed symmetrically and evenly over the distributor surface 13. A fraction of the milk film is caught between a first pair of knives 14, 15, each comprising a vertical knife section, 14a and 15a respectively and a horizontal knife section 14b and 15b respectively, extending from the vertical knife sections in the direction of the central axis of the first tube 10. The knives 14 and 15 define a knife angle the size of which determines the sampling ratio. If the angle for instance is 20° the sampling ratio will be 20 : 360 = 1 : 18, which is a very suitable value. The part of the milk film caught by the sampling funnel formed between the knives 14, 15 flows through a normally open valve 16 into the collection cup 7. In the present example it means that 1/18 of the milk flows into the collection cup 7, while the rest of the milk leaves the chamber 2 through a discharge tube 17 in the bottom of the chamber 2. The discharge tube 17 is connected to the milk line 3 or a milk tank and to the vacuum source.

The restriction 11 at the end of the tube 10 serves to increase the flow rate and thus to improve the spreading over the distributor plate 13 at low milking speeds and consequently increase the metering accuracy under the most unfavourable milking conditions. The restriction, however, must not be too narrow (not below 10 mm in diameter) because then it would cause a too great pressure drop over the apparatus with the result that the teat cups might fall off during milking.

The distributor surface 13 is relatively small, for example 20 mm in diameter, so that the liquid particles will not lose much of their speed by the friction against the distributor surface 13. High particle speed also improves the measuring accuracy.

Contrary to what was the case in the previously known apparatus the milk here leaves the distributor surface 13 completely before hitting the knives 14, 15 for sampling. It has been found according to the invention that a much greater measuring accuracy than obtainable in the known apparatus will be achieved when the knives do not form an integral part of the distributor surface. This can be observed specifically at low milking speed and large quantity of air when the apparatus according to the invention measures with accuracy of 1–2%, while the known apparatus show errors of over 10%.

The milk sample collected in the collection cup 7, which is proportional to the yield, is relatively large (for instance 1/18 of the yield) so that the sampling is practically speaking independent of the milking conditions such as milking rate, quantity of air, foaming, viscosity and vacuum. The first milk drawn from the cow is poor in fat while the last milk drawn in the milking is rich in fat, but the sample being collected all along the milking process it will be representative of the average fat percentage. On completion of the milking a secondary sampling is carried out in which all the milk from the collection cup is sucked up through a second tube 18 and flows into the interior of the chamber 2. The secondary sampling is started by closing the valve 16. The movable member of this valve is disposed on one end of a rocker arm 19 the other end of which is connected at one end of a rod 20 which with a certain clearance is carried through a tube 21 connecting the collection cup with the atmosphere. On the other end of the rod 20 is attached an operating knob by means of which the rod 20 can be pressed down against the action of a spring 23. Hereby the normally open valve 16 will be closed, and a sealing member 24 mounted at the lower end of the rod 20 and normally adapted to cut off the communication between the interior of the collection cup and the atmosphere by abutment against the lower end of the tube 21, will be removed from the tube 21 so that atmospheric air enters the collection cup 7 through the tube 21 and keeps the valve 16 closed until all milk in the collection cup 7 has been pressed through the second tube 18 by the incoming air.

Figure 4:
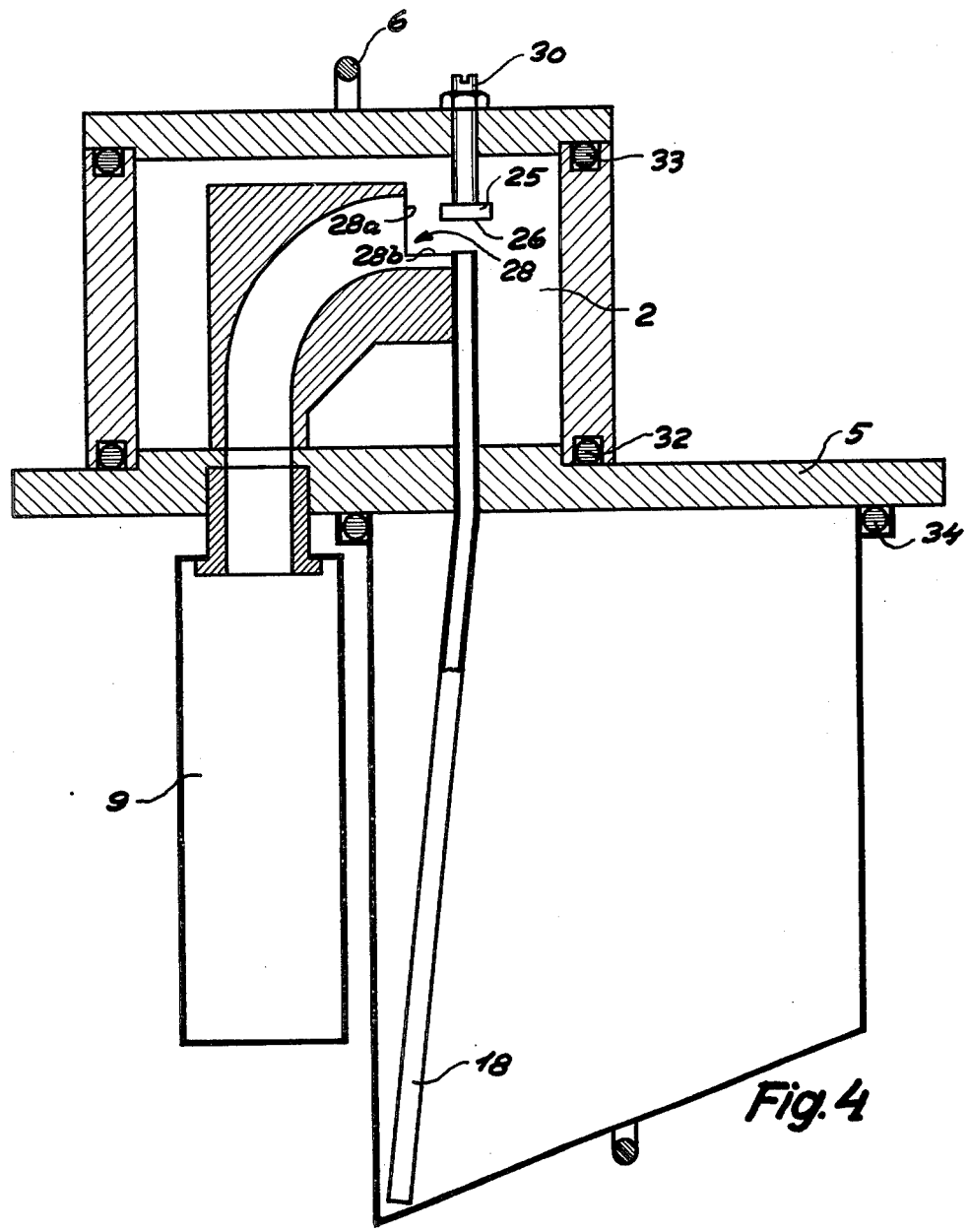
Figure 5:
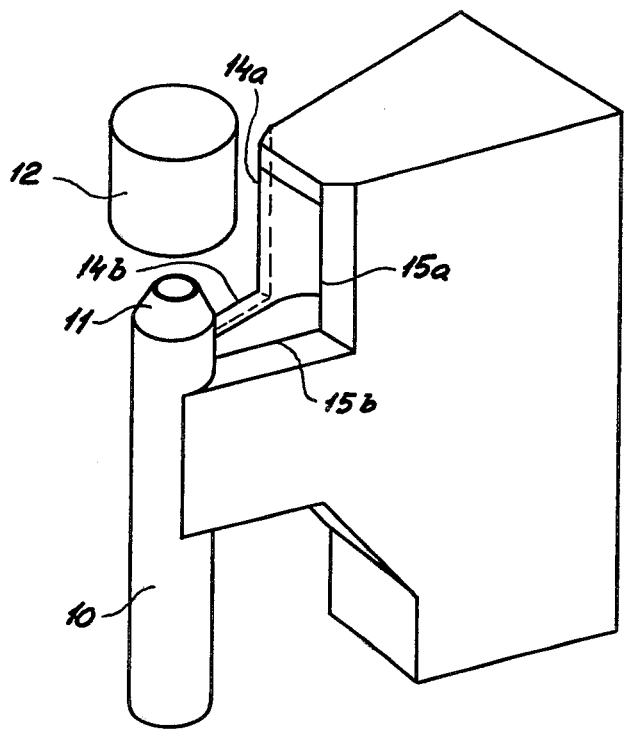
FIG. 5 presents a perspective view of part of the primary sampling system of the apparatus.
Figure 6:
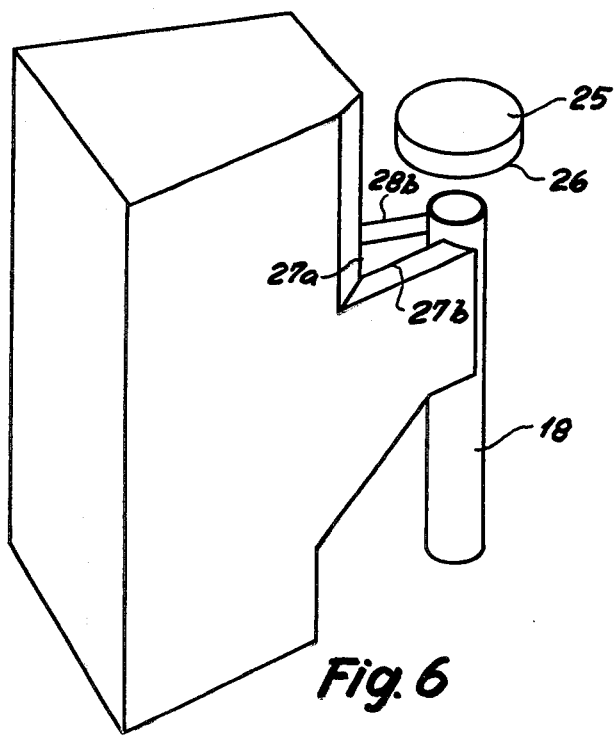
FIG. 6 presents a perspective view of part of the secondary sampling system of the apparatus.

As shown in greater detail in FIG. 4, the milk flows upwards through the tube 18 and the milk jet hits a second circular cylinder 25 the underside of which forms a second circular distributor surface 26. There the milk jet spreads to form a film distributed evenly and symmetrically over the distributor surface 26. A fraction of the milk film is caught between a second pair of knives 27, 28 each comprising a vertical knife section, 27a and 28a respectively, and a horizontal knife section, 27b and 28b respectively, extending from the vertical knife sections in the direction towards the central axis of the second tube 18. The knives 27 and 28 define a knife angle the size of which determines the secondary sampling ratio. If this knife angle, as in the primary sampling, is 20° the same sampling ratio of 1 : 18 will be obtained, so that the secondary sample collected in the sampling cup 9 detachably secured by the bayonet clamp under the plate 5 will be about 3.1 g of milk per kg yield from the cow, which is a suitable quantity for transport and laboratory testing (fat determination). The part of the milk from the collecting cup 7 which is not caught between the knives 27, 28 passes into the chamber 2 and is sucked away through the discharge tube 17.

It will be convenient that the two knife systems 14, 15 and 27, 28 are entirely identical so that the same casting mold can be used in the manufacture. After molding the knife systems including the funnels are glued to the base plate 5.

The second distributor surface 26 is slightly inclined, for instance 2° from the horizontal plane. This causes a slight asymmetry in the distribution of the milk leaving the distributor surface. By turning the distributor surface within 180° about the vertical axis of the cylinder 25 the secondary sampling ratio may be slightly varied to provide for production tolerances. The said 2° inclination of the distributor surface will produce a variation of about 12% in the sampling, and this is sufficient. The distributor surface is so arranged that the sampling is performed in the center of the adjustment range and a relative variation of ± 6% obtained. The adjustment is carried out by means of a vertical rod 30 provided with a notch and secured in the center of the circular upper surface of the cylinder 25, extending airtight through a close-tolerance hole in the cover of the chamber 2. This kind of adjustment is only feasible because the sampling funnel is not, as in the known apparatus, an integrated member of the distributor surface.

Theoretically the adjustment may be made in the primary sampling instead, but it has been found that the measurement would then be slightly more dependent on the milking rate and the velocity of the air than where the distributor surface is perfectly horizontal. The secondary sampling is independent of milking conditions and the greatest accuracy therefore is obtained by performing the adjustment there.

The apparatus is most critical to inclination in a plane parallel to the sectional plane in FIG. 3 or FIG. 4. If the apparatus inclines towards the sampling funnels in the sample will be larger, and vice versa if it inclines the otheer way. The apparatus is suspended on the milk line 3, as previously described, by means of the suspension clamp 4 and two hooks 4a, 4b. Contrary to the apparatus of the prior art the present apparatus is suspended so that the direction from the tubes 10, 18 to each of the sampling funnels 14, 15 and 27, 28 is parallel to the milk line 3. Moreover, the sampling funnels 14, 15 and 27, 28 are disposed on either side of the respective tubes 10, 18. Thus an error of inclination in one sampling, if for instance the milk line 3 is not perfectly horizontal, will be compensated by a reverse error of inclination in the second sampling. Complete compensation, however, will only be obtained if the flow rates from the two tubes 10 and 18 are the same, as is the case at normal milking speed. The measurement will therefore still to some extent depend on the inclination of the plane parallel to the milk line 3, but since the milk line, as already mentioned, is always approximately horizontal there will in actual practice arise only very small measuring errors caused by the fact that the apparatus in many milking parlours is to be dismantled after milking and suspended anew at the next cow to be milked.

To avoid milk from the primary sampling interfering with the secondary sampling a screen 31 has been interposed under the cover of the chamber 2 between the two sampling systems.

To provide the necessary seal, O-rings 32,33 and 34 respectively, are inserted between the cylindrical wall of the chamber 2 and the base plate 5, between the said wall and the cover, and between the collection cup 7 and the base plate.

What I claim is:

1. An apparatus for taking out an average sample of milk proportional to the yield from the milking of a cow and comprising
   a. a primary sampling system with a chamber into which the milk is sucked during the milking of the cow through a first tube terminating at a distance from a superimposed circular cylinder the bottom of which forms a substantially horizontal circular distributor surface which spreads the milk to form a film of which a fraction is caught between a first pair of knives, which are not integral with the distributor surface, and passed through a normally open valve into a collecting cup, while the major part of the milk leaves the chamber through a discharge tube in the bottom of the chamber, and
   b. a secondary sampling system which is adapted on completion of the milking to suck the milk from the collecting cup upwards into the chamber through a second tube extending from the bottom of the collecting cup and terminating at a distance from a superimposed second circular cylinder the bottom of which forms a second substantially horizontal circular distributor surface which spreads the milk to form a film of which a fraction is caught between a second pair of knives, which are not integral with the second distributor surface, and led down into a test cup, while the major part of the milk from the collecting cup leaves the chamber through the discharge tube in the bottom of the chamber.

2. An apparatus according to claim 1, and in which the first pair of knives are designed to form a first sampling funnel, each knife comprising a vertical knife section and a horizontal knife section extending from the lower end of the vertical knife section towards the first tube.

3. An apparatus according to claim 1 and wherein the second pair of knives are designed to form a second sampling funnel, each knife comprising a vertical knife section and a horizontal knife section extending from the lower part of the vertical knife section towards the second tube.

4. An apparatus according to claim 2 in which the normally open valve comprises a fixed valve seat at the bottom of the first sampling funnel and a valve member which is movable against the seat for closing the valve.

5. An apparatus according to claim 4 in which the movable valve member is so disposed on one end of a rocker arm that the valve is closed by pressing down one end of a rod against the action of a spring, the other end of the rod being secured to the other end of the rocker arm.

6. An apparatus according to claim 5 in which the rod is carried with a clearance through a tube by which the collecting cup communicates with the atmosphere and in which a sealing member mounted on the rod is adapted to seal off the connection between the interior of the collecting cup and the atmosphere when the valve is in its normal open position and to open the said connection when the rod is pressed down against the action of the spring to close the valve whereby air will flow in between the rod and the surrounding tube and keep the movable valve member pressed against the valve seat, while simultaneously the resulting pressure increase in the collecting cup automatically causes the milk therein to be pressed through the second tube to effect the second sampling which is finalized by air penetrating through the second tube into the chamber and reopening the valve.

7. An apparatus according to claim 1, wherein the first pair of knives are designed to form a first sampling funnel, each knife comprising a vertical knife section and a horizontal knife section extending from the lower end of the vertical knife section towards the first tube, and wherein the second pair of knives are designed to form a second sampling funnel, each knife comprising a vertical knife section and a horizontal knife section extending from the lower part of the vertical knife section towards the second tube, which apparatus is suspended on a milk line or vacuum line extending horizontally in the milking parlour so that the direction from the vertical symmetrical plane of each sampling funnel to the respective first or second tube of the sampling funnel is parallel to the milk or vacuum line, the direction from the first tube to the first sampling funnel being parallel to the direction from the second sampling funnel to the second tube so that the sampling funnels are disposed opposite one another.

8. An apparatus according to claim 7 in which at least one of the distributor surfaces is given a slight inclination, for instance 2° from the horizontal plane, and is rotatable about the axis of the respective cylinder.

9. An apparatus according to claim 8 in which the distributor surface of the secondary sampling system is given a slight inclination, for instance 2° from the horizontal plane, and is rotatable about the axis of the respective cylinder.

10. An apparatus according to claim 7 in which the two sampling funnels including the knives are of identical design.

11. An apparatus according to claim 10 in which the knives in each sampling funnel define a knife angle of 20° corresponding to the sampling of an amount in each system of 1/18 of the volume of milk.

* * * * *